United States Patent
Mazzola et al.

(10) Patent No.: US 11,867,679 B2
(45) Date of Patent: *Jan. 9, 2024

(54) INTEGRATION AND ACTIVE FLOW CONTROL FOR ENVIRONMENTAL SENSORS

(71) Applicant: Aclima Inc., San Francisco, CA (US)

(72) Inventors: Salvatore Mazzola, San Francisco, CA (US); Bassam Samih Dgheim, San Francisco, CA (US); Davida Herzl, San Francisco, CA (US); Meghan Elizabeth Thurlow, San Francisco, CA (US)

(73) Assignee: Aclima Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/686,345

(22) Filed: Mar. 3, 2022

(65) Prior Publication Data

US 2022/0268750 A1 Aug. 25, 2022

Related U.S. Application Data

(63) Continuation of application No. 16/409,624, filed on May 10, 2019, now Pat. No. 11,307,186.

(51) Int. Cl.
*G01N 33/00* (2006.01)

(52) U.S. Cl.
CPC ..... *G01N 33/0075* (2013.01); *G01N 33/0032* (2013.01)

(58) Field of Classification Search
CPC .................. G01N 33/0075; G01N 33/0032
See application file for complete search history.

(56) References Cited

U.S. PATENT DOCUMENTS

| 9,528,957 B2 | 12/2016 | Scheffler |
| 10,054,534 B1 | 8/2018 | Nourbakhsh |

(Continued)

FOREIGN PATENT DOCUMENTS

| CN | 103994484 | 8/2014 | |
| GB | 2536975 A | * 10/2016 | ........... G01N 1/2273 |

(Continued)

OTHER PUBLICATIONS

JP-2001174373-A-translate (Year: 2001).*
CN103994484—English (Year: 2014).

*Primary Examiner* — Kristina M Deherrera
*Assistant Examiner* — Fatemeh Esfandiari Nia
(74) *Attorney, Agent, or Firm* — Van Pelt, Yi & James LLP

(57) ABSTRACT

A technique for monitoring and collecting environmental data is provided that supports acquisition and analysis of quality measurements of pollutants by sensors based on different technologies in an integrated manner. The system includes a primary substrate having a plurality of sensor modules, each sensor module configured to couple to a sensor, and a manifold having a plurality of flow hoods, each flow hood disposed on a top surface of a sensor and connected to another flow hood or component in the manifold. In some cases, the sensor modules are gas sensor modules, and the sensor is a gas sensor. The manifold thus provides a closed system through which a fluid sample can flow across a series of gas sensors in an actively controlled manner that enables independent flow control over each individual gas sensor while limiting exposure of the fluid sample to potential sources of contamination.

18 Claims, 11 Drawing Sheets

(56) References Cited

U.S. PATENT DOCUMENTS

| | | | |
|---|---|---|---|
| 11,009,474 B2 * | 5/2021 | Brahem | G01N 33/0047 |
| 11,169,239 B2 | 11/2021 | Mishra | |
| 2004/0158359 A1 | 8/2004 | Frecska | |
| 2005/0061056 A1 | 3/2005 | Sunshine | |
| 2005/0092065 A1 | 5/2005 | Tajima | |
| 2011/0138904 A1 | 6/2011 | Nakaso | |
| 2014/0250975 A1 * | 9/2014 | Kane | G01N 1/2205 |
| | | | 73/23.31 |
| 2014/0278186 A1 | 9/2014 | Herzl | |
| 2015/0039262 A1 | 2/2015 | Tan | |
| 2015/0153299 A1 | 6/2015 | Chou | |
| 2015/0369656 A1 | 12/2015 | Chen | |
| 2016/0081597 A1 | 3/2016 | Bhavaraju | |
| 2016/0165193 A1 | 6/2016 | Rasheed | |
| 2016/0370302 A1 | 12/2016 | Briden | |
| 2017/0160157 A1 | 6/2017 | Chang | |
| 2017/0187783 A1 | 6/2017 | Pogorelik | |
| 2017/0372601 A1 | 12/2017 | Yamashita | |
| 2018/0120278 A1 | 5/2018 | Hoorfar | |
| 2019/0137467 A1 | 5/2019 | Chou | |
| 2019/0324436 A1 | 10/2019 | Cella | |
| 2020/0284820 A1 | 9/2020 | Zhang | |
| 2020/0309678 A1 | 10/2020 | Tumpold | |

FOREIGN PATENT DOCUMENTS

| | | | |
|---|---|---|---|
| GB | 2559704 | | 8/2018 |
| JP | 2001174373 | | 6/2001 |
| JP | 2001174373 A | * | 6/2001 |
| JP | 2018128465 | | 8/2018 |
| WO | 2013130506 | | 9/2013 |
| WO | 2018089674 | | 5/2018 |

* cited by examiner

INTEGRATION AND ACTIVE FLOW CONTROL FOR ENVIRONMENTAL SENSORS

This application is a continuation of U.S. patent application Ser. No. 16/409,624, now U.S. Pat. No. 11,307,186, entitled INTEGRATION AND ACTIVE FLOW CONTROL FOR ENVIRONMENTAL SENSORS filed May 10, 2019 which is incorporated herein by reference for all purposes.

BACKGROUND OF THE INVENTION

Air quality is a measure of the condition of air relative to the requirements of human need or purpose. Air quality monitoring is performed to measure the levels of pollutants in the air so as to detect potential harmful air pollution. Depending on the application, air quality monitoring systems can be mobile or stationary and can be used in outdoor or indoor settings. Air quality monitoring typically includes detecting and taking measurements of pollutants or contaminants in the air such as nitrogen dioxide ($NO_2$), carbon monoxide (CO), nitrogen oxide (NO), ozone ($O_3$), sulphur dioxide ($SO_2$), carbon dioxide ($CO_2$), volatile organic compounds (VOCs), and particulate matter. These measurements are performed by various types of environmental sensors including gas sensors based on different technologies or methodologies. Existing systems do not currently support the acquisition of quality measurements of contaminants by multi-modality gas sensors based on different technologies in an integrated or cohesive manner.

BRIEF DESCRIPTION OF THE DRAWINGS

Various embodiments of the invention are disclosed in the following detailed description and the accompanying drawings.

DETAILED DESCRIPTION

Figure 1:
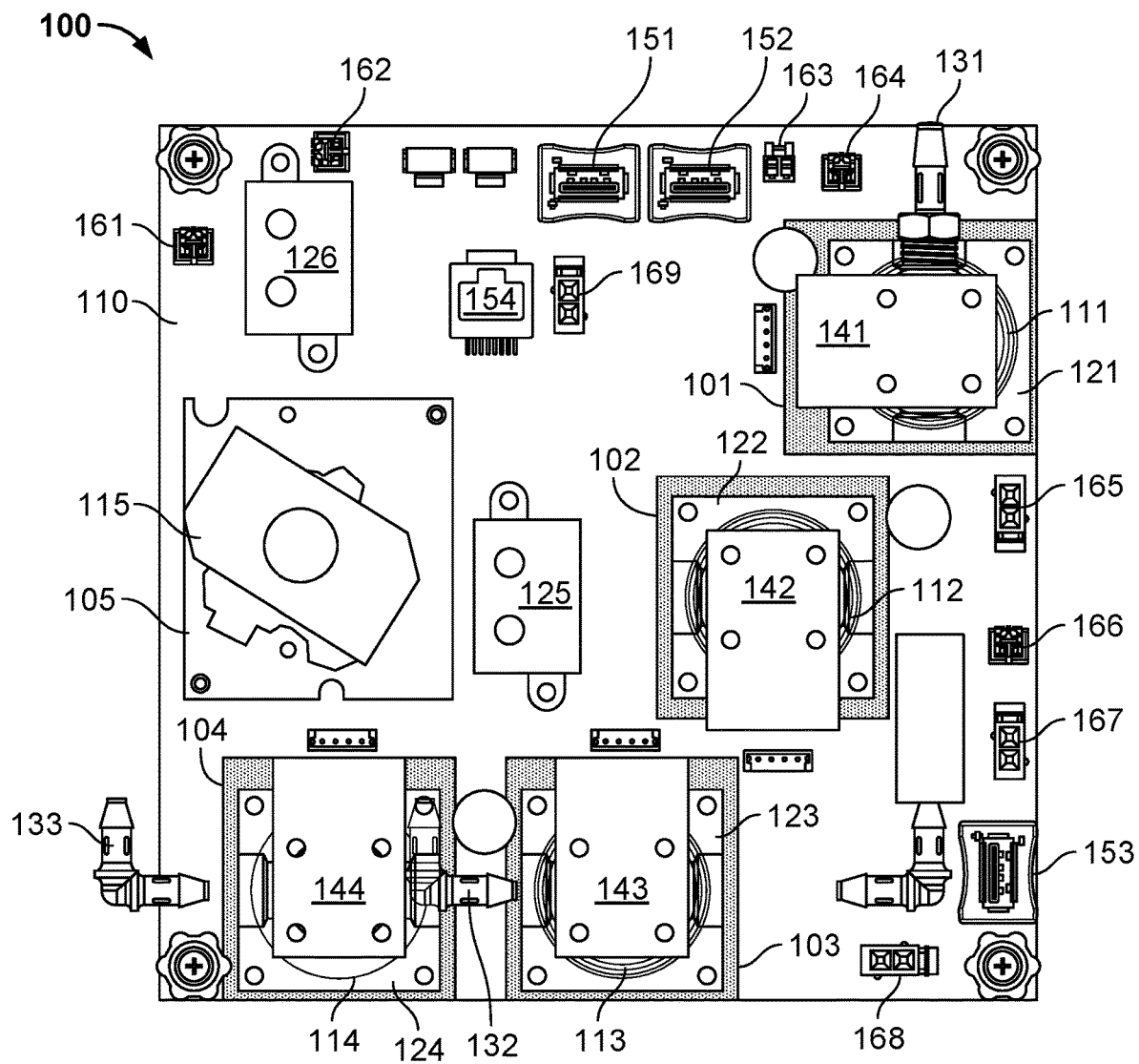
FIG. 1 shows a top view of an embodiment of a system for monitoring and collecting environmental data that supports the acquisition of quality measurements of contaminants or pollutants by sensors based on different technologies in an integrated manner.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Systems for monitoring air quality rely on the use of various sensors including different types of gas sensors to measure contaminants or pollutants in the air. Some of these pollutants are highly reactive and exist only in trace amounts in a typical air sample. Accordingly, depending on the pollutant desired to be measured, different types of environmental sensors including gas sensors that are based on different technologies or methodologies and have different sensitivities are employed. However, existing systems are unable to support the acquisition of quality measurements of contaminants or pollutants by gas sensors based on different technologies in an integrated and cohesive manner. In particular, different sensors are typically manufactured and provided for use on a single board designed to support a single sensor. This type of configuration does not provide electrical support, data support, and mechanical support on a central unit that allows integration of different sensors with different options to obtain and send sensor data for processing and analysis. Existing systems requiring separate boards for each sensor and separate systems of data collection make it difficult to collect different types of sensor data and to analyze collected data in a cohesive manner.

In some embodiments, a system for monitoring and collecting environmental data is provided that supports the acquisition of quality measurements of contaminants or pollutants by sensors based on different technologies in an integrated manner. The system includes a primary substrate comprising a plurality of sensor modules, wherein each sensor module is configured to couple to or engage with a sensor. The system also includes a manifold comprising a plurality of flow hoods, wherein each flow hood is configured to be disposed on a top surface of a sensor coupled to a sensor module on the primary substrate and wherein a flow hood in the manifold is configured to be connected to another component in the manifold or on the primary substrate. In some cases, connective tubing is used to couple or connect a flow hood with another flow hood, or to couple or connect one component (e.g., a flow hood) to another component (e.g., a flow meter). The manifold is configured to enable active and independent control of a fluid flow (e.g., an air sample) over at least some of the sensors disposed on the primary substrate. In particular, the manifold is configured to provide a closed system through which a fluid sample can flow across various sensors in a controlled manner that limits exposure of the fluid sample to the outside environment. In some instances, the sensors are gas sensors and the sensor modules are gas sensor modules.

Additionally, at least in some cases, the system includes a plurality of secondary substrates, wherein each secondary substrate is disposed on a top surface of a flow hood in the manifold. In some instances, each secondary substrate on a given flow hood is configured to capture an environmental metric at a sensor point corresponding to a location of the sensor (e.g., the gas sensor) on which the given flow hood is disposed. In some examples, the environmental metric comprises one or more metrics selected from the group consisting of pressure, temperature, and humidity. The system also includes a connector disposed on the primary substrate configured to provide a connection from a sensor module to a data processor. In some cases, the system includes a device connector configured to couple a device to the primary substrate. In some cases, the system is configured to connect to a device regardless of whether the device is physically disposed on or mounted to the primary substrate.

In some embodiments, a method for monitoring and collecting environmental data is disclosed that supports the acquisition of quality measurements of contaminants or pollutants by sensors based on different technologies in an integrated manner. The method includes: actively controlling a flow of fluid through a manifold comprising a plurality of flow hoods; collecting an environmental metric at a sensor point corresponding to a location of at least one sensor in a plurality of sensors, wherein the plurality of sensors are coupled to a primary substrate; and monitoring data obtained from at least one sensor in the plurality of sensors using a data processor. In some embodiments, each sensor in the plurality of sensors is coupled electrically or mechanically to the primary substrate.

In some examples, the manifold is configured to enable active and independent control of a fluid flow (e.g., an air sample) over at least one of the sensors disposed on the primary substrate. For instance, in some embodiments, at least one flow hood in the plurality of flow hoods is disposed on a top surface of at least one of the plurality of sensors coupled to a sensor module on the primary substrate. Additionally, a flow hood in the manifold is configured to be connected to another component in the manifold or on the primary substrate. This configuration provides a closed system through which a fluid sample can flow across a plurality of sensors (e.g., a series of gas sensors) in a controlled manner that limits exposure to the outside environment.

Additionally, at least in some instances, collecting an environmental metric at a sensor point corresponding to a location of at least one sensor in a plurality of sensors is performed using a plurality of secondary substrates, wherein each secondary substrate is disposed on a top surface of a flow hood in the manifold. In some embodiments, each secondary substrate on a given flow hood is configured to capture an environmental metric at a sensor point corresponding to a location of the sensor on which the given flow hood is disposed. In some examples, the environmental metric comprises one or more metrics selected from the group consisting of pressure, temperature, and humidity. In contrast to existing systems that rely on an external probe to measure an environmental metric such as temperature, pressure, or humidity, by using a secondary substrate located at a sensor point, the resulting measurements will be more accurate. As noted previously, in some instances, the sensors are gas sensors and the sensor modules are gas sensor modules.

FIG. 1 depicts a top view 100 of an embodiment of a system for monitoring and collecting environmental data that supports the acquisition of quality measurements of contaminants or pollutants by sensors based on different technologies in an integrated manner. In the example shown, the system includes a primary substrate 110 comprising a plurality of sensor modules. In this case, the plurality of sensor modules includes sensor modules depicted at 101, 102, 103, 104, and 105. Each sensor module in the plurality of sensor modules is configured to couple to a sensor. In some cases, as described in more detail below, each sensor module is configured to mechanically and electrically couple to a sensor. For example, although not visible in FIG. 1, each sensor module includes an area (e.g., a recessed area or slot) configured to couple to or engage with a particular sensor (e.g., by mounting or inserting the sensor on or into a recessed area or slot). An exemplary embodiment depicting a plurality of sensor modules is discussed in more detail below with respect to FIG. 6.

Returning to FIG. 1, a plurality of sensors (depicted at 111, 112, 113, 114, and 115 respectively) are disposed on the primary substrate 110, each sensor in the plurality of sensors being coupled to a sensor module on the primary substrate. In particular, sensor 111 is coupled to sensor module 101, sensor 112 is coupled to sensor module 102, sensor 113 is coupled to sensor module 103, sensor 114 is coupled to sensor module 104, and sensor 115 is coupled to sensor module 105.

In some examples, the sensor (e.g., sensor 111, sensor 112, sensor 113, sensor 114, and sensor 115) disposed on the primary substrate 110 is selected from a group consisting of multi-modality gas sensors. Multi-modality gas sensors comprise different types of gas sensors both in terms of the type of gas or substance measured (e.g., nitrogen dioxide ($NO_2$), carbon monoxide (CO), nitrogen oxide (NO), oxygen ($O_2$), ozone ($O_3$), sulphur dioxide ($SO_2$), carbon dioxide ($CO_2$), volatile organic compounds (VOCs) and particulate matter) and the different technologies or methodologies of sensor types (e.g., metal oxide, electrochemical (EC), optical, gas sensitive semiconductor (GSS), photoionization detector (PID), and non-dispersive infrared (NDIR)) depending on the type of gas or substance measured.

The system as shown in FIG. 1 provides an ability to integrate different types of devices or sensors on to a single primary substrate (e.g., primary substrate 110). In particular, each sensor module depicted at 101, 102, 103, 104, and 105 of FIG. 1 is configured to couple to a sensor technology type. For instance, a given sensor module can be configured to couple to a particular sensor technology type such as a metal oxide sensor type including for example, a gas sensitive semiconductor or GSS technology. This configuration provides for the coupling of any GSS gas sensor (e.g., for detecting the presence of a particular gas such as nitrogen dioxide, carbon monoxide, or nitrogen oxide) via the gas sensor module to the primary substrate. Alternatively, a given sensor module can be configured to couple to a different technology of gas sensor such as PID, NDIR, or electrochemical. Each of these configurations provides for the coupling of other types of sensors that detect other gases or substances including, for example, volatile organic compounds, carbon dioxide and Temperature/Pressure/Relative Humidity.

The system further comprises one or more device connectors (e.g., power or data connectors) disposed on the primary substrate 110. Each connector is configured to couple or connect a device to the primary substrate 110 or to provide a connection from a sensor module to a data processor. In particular, as described in further detail below, the primary substrate 110 includes USB hubs, inputs, or connectors capable of supporting or connecting almost any sensing device to allow integration of any device or sensor that runs over USB or any other communications protocol that could emerge in the future. Accordingly, the system is configured to support, control, and integrate data collected from external devices including sensors that may not be physically mounted on the primary substrate 110.

For example, data connectors (e.g., USB connectors depicted at 151, 152, and 153 and Ethernet connector at 154) provide an ability to make a data connection to a data processor or a processing unit (not shown) or to a sensor (e.g., a particulate matter sensor). The data processor or processing unit is configured to receive and process data obtained from various sensors and other devices coupled (e.g., electrically or mechanically) to the primary substrate 110. Additionally, power connectors depicted at 161, 162, 163, 164, 165, 166, 167, 168, and 169 are used to provide power to devices (e.g., gas pumps, processors, or sensors). In this manner, the system is configured to electrically couple and to provide data connections to various devices (e.g., USB or Ethernet devices) even if such devices are not mechanically disposed on or physically mounted or coupled directly to the primary substrate 110. In the example shown, the system is configured to provide a data connection to a particulate matter sensor (not shown) via data connector 153 and power to the particulate matter sensor via power connector 168. The system is also configured to provide a data connection to an ozone sensor (not shown) via data connector 154 and power to the ozone sensor via power connector 169.

One challenge in monitoring and collecting environmental data, especially in a mobile application, is to obtain a high quality air sample that can be tested and measured appropriately to detect a given pollutant or contaminant that is highly reactive, sensitive, or present in very small trace amounts. In these cases, higher quality measurements will be obtained from gas sensors if the air sample is conditioned and if its flow provided to each gas sensor is controlled.

Accordingly, as shown in FIG. 1, the system includes manifold comprising a plurality of flow hoods configured to enable active and independent control of a fluid flow (e.g., an air sample) over at least some of the sensors, which as described above can be selected from a group consisting of multi-modality gas sensors, disposed on the primary substrate. In the case where the sensors are gas sensors, each flow hood (e.g., depicted at 121, 122, 123, and 124) is configured to be disposed on a top surface of at least one of the gas sensors coupled to a gas sensor module on the primary substrate 110. In particular, each flow hood coupled to a gas sensor provides a sealed chamber that allows the pushing or pulling of a fluid (e.g., an air sample) through a controlled volume over the sensor.

The fluid enters each flow hood through an input port and leaves each fluid port through an output port. In some cases, a fitting is used at the input and output ports to attach or couple connective tubing that accommodates a flow of the fluid through the manifold. In this manner, the manifold is configured to provide active flow control of a fluid flow by pushing or pulling a fluid across a top surface of a gas sensor through a flow hood disposed on the top surface of the gas sensor. In the case where a plurality of gas sensors are used, the manifold is configured to provide active flow control of a plurality of fluid flows by pushing or pulling a fluid across a top surface of each of a plurality of gas sensors through a flow hood disposed on the top surface of each of the plurality of gas sensors. Additionally, each of the fluid flows across a given gas sensor can be adjusted based at least in part on a type or sensitivity of the given gas sensor.

Certain gases are more reactive than other gases or are present in very small or trace amounts in the acquired air sample. For highly reactive gases such as nitrogen dioxide ($NO_2$) and nitrogen oxide (NO), it is important to condition the air sample obtained in order to limit exposure to components that might react with the gas desired to be measured. Accordingly, in some embodiments for these highly reactive gases, the fluid flow (e.g., air sample) can be pulled to a particular gas sensor) whereas for a less reactive gas such as carbon dioxide ($CO_2$), the fluid flow (e.g., air sample) can be pushed to a particular gas sensor.

In some cases, a pump system provides active control of a fluid flow through the manifold and across the face or top surface of each gas sensor. In particular, the pump system is configured to independently either pull or push a fluid sample across the face or top surface of a given gas sensor through a flow hood disposed on the top surface of the given gas sensor. Thus, the fluid sample flows through the manifold via a plurality of flow hoods disposed on the top surface of a plurality of gas sensors, wherein the flow hoods are connected to each other (e.g., via connective tubing and fittings) and to other components to form the manifold.

In some embodiments, the pump system includes a plurality of pump units, each pump unit having a vacuum side and a pressure side to either pull or push a fluid across a top surface of a gas sensor. For example, to pull a fluid flow across a top surface of a given gas sensor, a pump unit is positioned on a backside of the sensor to draw air towards the sensor from the backside of the sensor. Alternately, to push a fluid flow across a top surface of a given gas sensor, a pump unit is positioned on a front side of the given gas sensor to push or blow air through the manifold towards the gas sensor. In this manner, the system is configured to either push or pull a fluid flow across a top surface of a given gas sensor based at least in part on a type or sensitivity of the gas sensor and regardless of the gas sensor's flow order or flow sequence along the manifold.

The configuration of a plurality of flow hoods as described herein, wherein each flow hood is disposed over a gas sensor and connected (e.g., via connective tubing and fittings) to provide a manifold, allows for a conditioned air sample to be provided to each gas sensor by limiting the volume of fluid (via the flow hood) that passes over each sensor. This results in a more laminar air flow across a top surface of a sensor as opposed to existing systems that merely allow air to diffuse over the sensor without controlling the amount of air sample or actively controlling the air flow.

Additionally, each flow hood in the manifold is configured to be connected to another component (e.g., a flow hood or a flow meter) in the manifold (e.g., via connective tubing (not shown)) that allows for a fluid (e.g., an air sample) to flow through each flow hood in the manifold. Fluid flow is actively and independently controlled by either pushing or pulling the fluid (e.g., via a fluid pump) over a given sensor through the flow hood disposed on a top surface of the given sensor. In the example shown, flow hood 121 is disposed on a top surface of gas sensor 111, flow hood 122 is disposed on a top surface of gas sensor 112, flow hood 123 is disposed on a top surface of gas sensor 113, and flow hood 124 is disposed on a top surface of gas sensor 114. In some cases, the connective tubing is attached via a fitting (e.g., depicted at 132 and 133) coupled to the flow hood. A fitting is also used to attach connective tubing to a fluid input (e.g., depicted at 131) through which a fluid is received into the manifold or a fluid output (not shown) through which a fluid is released from the manifold.

As described above, the flow of fluid is actively controlled by either pushing or pulling the fluid through each flow hood in the manifold, wherein a flow hood is configured to be connected to another flow hood or to another component in the manifold or on the primary substrate (e.g., via connective tubing attached with fittings to each of the flow hoods). In this manner, the system is configured to enable control of a fluid flow over a plurality of gas sensors such that the fluid sample reaches each gas sensor in a selected or particular flow order or flow sequence.

Certain considerations guide how various gas sensors are positioned on the board and the mechanical layout of components on the board. As discussed above, one consideration is whether the gas being measured is highly reactive and requires a conditioned air sample. For example, for a pollutant that is highly reactive or unstable in an air sample (e.g., ozone or $NO_2$), the more quickly and cleanly the air sample can be provided to the gas sensor, the higher the quality of the resulting measurement. Thus, it is advantageous to pass the air sample first to the gas sensors measuring highly reactive pollutants before the pollutant dissipates or the air sample is exposed to any other components that might react with the pollutant as the air sample flows through the manifold.

To accomplish this result, rather than allowing air to simply diffuse over a sensor, the air sample is provided to selected sensors in a particular order and in a controlled volume via a manifold that provides as little space as possible over the face of the sensor while providing sufficient sample to enable a high quality measurement for accurate testing.

In some cases, the order of the gas sensors on the primary substrate is determined based at least in part on the reactivity of each pollutant to be measured. For example, the gas sensors and manifold are configured in a mechanical layout on the primary substrate such that the fluid flow across a top surface of each gas sensor as determined by the manifold reaches the gas sensors in an order from those measuring the most reactive gases to those measuring the least reactive gases. The air sample is provided as quickly and cleanly as possible to the sensors measuring the most reactive gases that will be more sensitive to the purity of the air sample. By selecting a position of each gas sensor on the primary substrate and by configuring the fluid flow through the manifold through a choice of how each flow hood is connected to other components in the manifold, the system can be used to dictate a flow order or flow sequence of a fluid sample over a series of different gas sensors. Better measurements are obtained by prioritizing or ordering the gas sensors in a hierarchy from those measuring the most reactive to the least reactive pollutants. The system provides active control of the fluid flow via the manifold and based on the application. The system thus accommodates the different natures of certain gases or substances (e.g., different reactivity or sensitivity) by providing a choice of placement of a gas sensor measuring a particular gas in a certain flow order as dictated by the manifold.

As described above, the ability provided by the system of dictating, setting, or establishing a flow order or flow sequence of a fluid sample over a series of different gas sensors provides an advantage in certain applications that require measuring gases that vary in terms of their reactivity or sensitivity, or in the relative amount that they are present in the air sample. In particular, gas sensors for highly reactive or sensitive gases or for gases present in trace amounts are positioned to receive a fluid sample at an earlier point in the flow order or position in the flow sequence, while gas sensors for less reactive or sensitive gases or gases present in relatively large amounts in the fluid sample are positioned to receive the fluid sample at a later time or position in the flow sequence.

In some embodiments, the manifold is configured to provide a conditioned air sample across a top surface of each of the gas sensors via active control of a fluid flow through each flow hood. Here, in order to obtain a high quality measurement, it is desirable to provide a more laminar flow such that the fluid flows across a face or top surface of the gas sensor in a parallel direction as opposed to flowing in a direction that is perpendicular to the face or top surface of the sensor. To generate or produce a more laminar flow across the face or top surface of the gas sensor, the manifold is configured to provide a small, closed, and controlled volume (e.g., via each flow hood disposed on a top surface of a gas sensor) to ensure the space over each gas sensor through which the fluid flows is as small as possible while still being sufficient to provide an accurate measurement.

Using a pump system, the manifold is also configured to provide independent control of a fluid flow across a top surface of a gas sensor by either pulling or pushing the fluid across a top surface of a given gas sensor, which can be adjusted based on a type or sensitivity of the given gas sensor (e.g., the reactivity of the gas being measured by the given gas sensor). For example, in the case of measuring a highly reactive and unstable pollutant, pushing an air sample will cause at least some of the highly reactive and unstable pollutant in the air sample to be lost. Accordingly, in this case, the manifold is configured to pull air towards the sensor for measuring the highly reactive and unstable pollutant, providing the air sample to the sensor before it is exposed to any other components, pumps, or mechanical structures that might compromise the air sample.

Certain gas sensors are also sensitive to a flow rate and direction of flow of a fluid sample. A response of the gas sensor can be dependent on the rate of the fluid flow received across the face of the gas sensor. For example, a fluid that is flowing at a rate of one liter per minute across the face of the gas sensor produces a different response or measurement as compared to a fluid flowing at a rate of half a liter per minute. For this reason, to ensure an accurate and consistent set of measurements, it is important to provide a consistent and steady fluid flow across a gas sensor disposed on the primary substrate.

Accordingly, conditioning the air sample includes ensuring that a consistent and steady flow is provided. Here, the manifold includes a plurality of low flow hoods configured to provide a consistent and steady fluid flow across a gas sensor disposed on the primary substrate. Using this configuration of flow hoods confines the fluid sample to a smaller region that provides a small amount of volume over the sensor that is sufficient for the gas sensor to make a quality measurement and also helps to provide a more laminar flow across the face of the gas sensor. Additionally, the small amount of volume provided by the disclosed flow hoods facilitates measurements of fluid flows that are very low (e.g., as low as half a liter per minute) in contrast to industry standards, which in this case are already set at relatively low flow rates (e.g., two liters per minute). The flow hoods of the disclosed manifold are also configured to minimize the amount of fluid flow needed to pass through the manifold to provide a sufficient amount of sample to the various gas sensors disposed under each flow hood, which is of particular importance in a mobile application where spatial data is critical.

In some instances, and in particular, in cases where a consistent and steady flow is advantageous, the system is configured to monitor or measure the fluid flow through the manifold using a flow measurement device such as a flow meter. As shown in FIG. 1, the system includes one or more flow meters (e.g., depicted at 125 and 126 respectively) that can be used to measure a flow of fluid through the manifold. In some cases, the system is configured to push or pull a fluid flow from a flow hood disposed on a top surface of a gas sensor to a particular flow meter. The flow meter is configured to measure a flow of fluid. The fluid that has passed though the flow meter can then be pushed or pulled to a subsequent flow hood disposed on a top surface of another gas sensor. In some embodiments, the pump system is used to control or provide a steady flow of fluid through the manifold.

As shown in FIG. 1, the system also includes a plurality of secondary substrates (e.g., depicted at 141, 142, 143, and 144). In this case, each secondary substrate is disposed on a top surface of a flow hood in the manifold. In the example shown, secondary substrate 141 is disposed on a top surface of flow hood 121, secondary substrate 142 is disposed on a top surface of flow hood 122, secondary substrate 143 is disposed on a top surface of flow hood 123, and secondary substrate 144 is disposed on a top surface of flow hood 124. In some instances, each secondary substrate on a given flow hood is configured to capture an environmental metric at a sensor point corresponding to a location of the sensor on which the given flow hood is disposed. In some cases, as described in more detail below, the secondary substrate is a printed circuit board configured to provide temperature, pressure, or humidity measurements. In contrast to existing systems that rely on an external probe to measure an environmental metric such as temperature, pressure, or humidity, by using a secondary substrate located at a sensor point, the resulting measurements will be more accurate.

Figure 2:
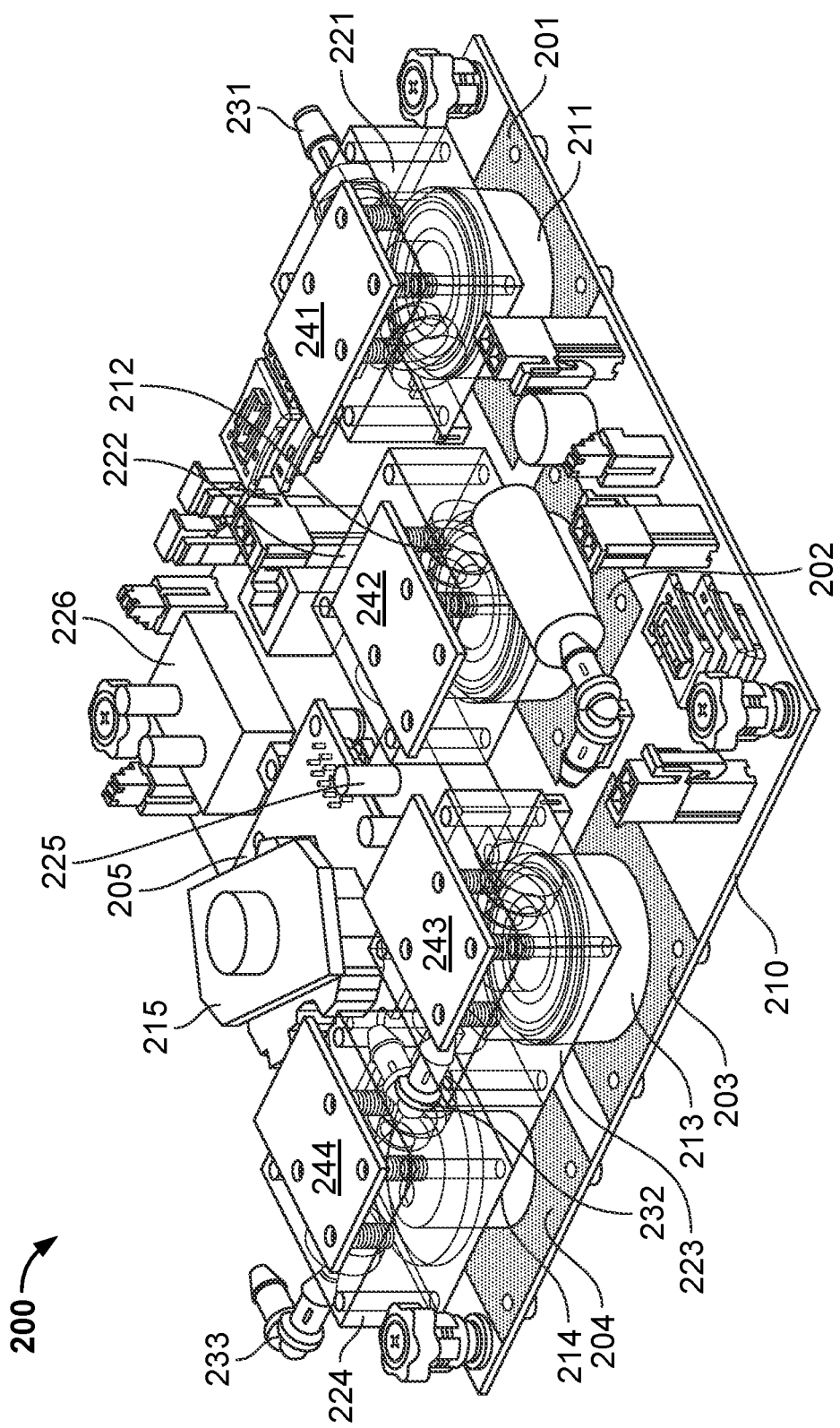
FIG. 2 shows a perspective view of an embodiment of the system of FIG. 1 for monitoring and collecting environmental data.

FIG. 2 depicts a perspective view 200 of an embodiment of the system of FIG. 1 for monitoring and collecting environmental data that supports the acquisition of quality measurements of contaminants or pollutants by sensors based on different technologies in an integrated manner.

FIG. 2 depicts the components shown in FIG. 1 in a view that illustrates how certain components are disposed or stacked on top of each other.

As shown in FIG. 2, the system includes a primary substrate 210 comprising a plurality of sensor modules (depicted here at 201, 202, 203, 204 and 205). Each sensor module in the plurality of sensor modules is configured to couple to a sensor. A plurality of sensors (depicted at 211, 212, 213, 214, and 215 respectively) are disposed on the primary substrate 210, each sensor in the plurality of sensors being coupled to a sensor module on the primary substrate. Here, sensor 211 is coupled to sensor module 201, sensor 212 is coupled to sensor module 202, sensor 213 is coupled to sensor module 203, sensor 214 is coupled to sensor module 204, and sensor 215 is coupled to sensor module 205. As described above with respect to FIG. 1, the various sensors can be selected from a group consisting of multi-modality gas sensors that measure different types of substances and include different technologies.

Also depicted in FIG. 2 is a manifold comprising a plurality of flow hoods configured to enable active and independent control of a fluid flow (e.g., an air sample) over at least some of the gas sensors disposed on the primary substrate 210. Here, each flow hood (e.g., box-shaped transparent components depicted at 221, 222, 223 and 224) is shown in FIG. 2 to be disposed on a top surface of a gas sensor coupled to a gas sensor module on the primary substrate 210. As described above, each flow hood coupled to a gas sensor provides a sealed chamber that allows the pushing or pulling of a fluid (e.g., an air sample) through a controlled volume over the sensor, which provides a more optimally conditioned air sample to the sensor by limiting the volume of fluid (using the flow hood) that passes over each sensor resulting in a more laminar air flow across a top surface of each sensor.

Each flow hood in the manifold is configured to be connected to another flow hood or to another component in the manifold or on the primary substrate (e.g., via connective tubing (not shown) and fittings) that allows for a fluid (e.g., an air sample) to flow through each flow hood in the manifold. Fluid flow is actively and independently controlled by either pushing or pulling the fluid (e.g., via a fluid pump) over a given sensor through the flow hood disposed on a top surface of the given sensor.

As shown in FIG. 2, flow hood 221 is disposed on a top surface of gas sensor 211, flow hood 222 is disposed on a top surface of gas sensor 212, flow hood 223 is disposed on a top surface of gas sensor 213, and flow hood 224 is disposed on a top surface of sensor 214. In some cases, the connective tubing is attached via a fitting (e.g., depicted at 232 and 233) coupled to the flow hood. A fitting is also used to attach connective tubing to a fluid input (e.g., depicted at 231) through which a fluid is received into the manifold or a fluid output (not shown) through which a fluid is released from the manifold. In this manner, the system is configured to enable control of a fluid flow over a plurality of gas sensors such that the fluid sample reaches each gas sensor in a selected or particular flow order or flow sequence.

Additionally, as shown in FIG. 2, the system includes one or more flow meters (e.g., depicted at 225 and 226 respectively) that can be used to measure a flow of fluid through the manifold. In some cases, the system is configured to push or pull a fluid flow from a flow hood disposed on a top surface of a gas sensor to a particular flow meter. The flow meter is configured to measure a flow of fluid and can be used to ensure a consistent and steady fluid flow through the manifold. The fluid passed through the flow meter can then be pushed or pulled to a subsequent flow hood disposed on a top surface of another gas sensor.

The system also includes a plurality of secondary substrates (e.g., depicted at 241, 242, 243, and 244). In this case, each secondary substrate is disposed on a top surface of a flow hood in the manifold. In the example shown, secondary substrate 241 is disposed on a top surface of flow hood 221, secondary substrate 242 is disposed on a top surface of flow hood 222, secondary substrate 243 is disposed on a top surface of flow hood 223, and secondary substrate 244 is disposed on a top surface of flow hood 224. In some instances, each secondary substrate on a given flow hood is configured to capture an environmental metric at a sensor point corresponding to a location of the sensor on which the given flow hood is disposed. In some cases, as described in more detail below, the secondary substrate is a printed circuit board configured to provide temperature, pressure, or humidity measurements. In contrast to existing systems that rely on an external probe to measure an environmental metric such as temperature, pressure, or humidity, by using a secondary substrate located at a sensor point, the resulting measurements will be more accurate.

Figure 3:
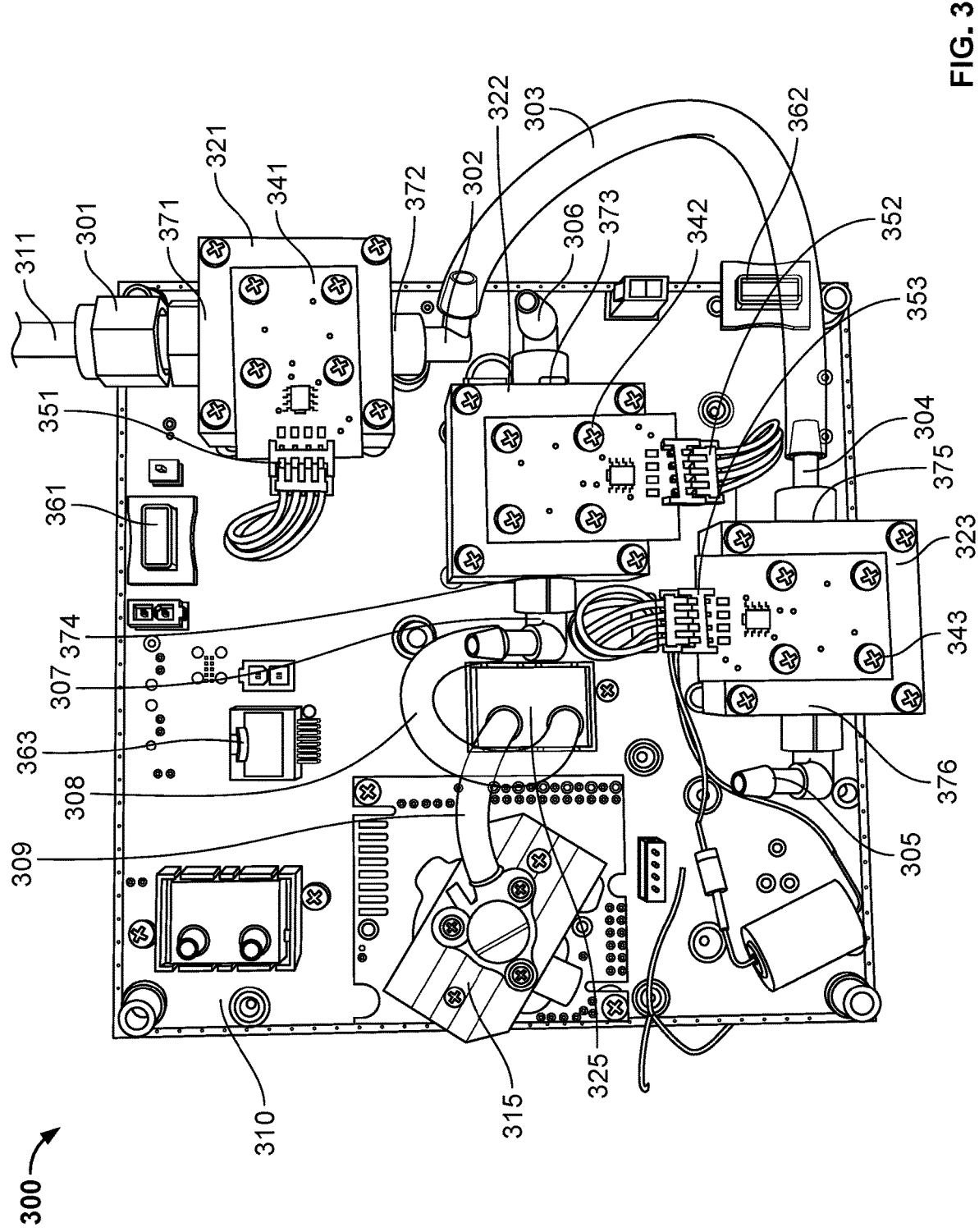
FIG. 3 shows a top view of an exemplary embodiment of a system implementing at least some of the components depicted and described with respect to FIGS. 1 and 2.

FIG. 3 shows a top view 300 of an exemplary embodiment of a system implementing at least some of the components depicted and described with respect to FIGS. 1 and 2 above. As shown in FIG. 3, the system includes a primary substrate, which in this case is a printed circuit board 310 having a plurality of gas sensor modules. As described above, each gas sensor module is configured to couple to a gas sensor. In this example, the gas sensor modules are configured to couple to gas sensors that detect or measure nitrogen dioxide ($NO_2$), carbon monoxide (CO), nitrogen oxide (NO), volatile organic compounds (VOCs), and carbon dioxide ($CO_2$).

The system shown in FIG. 3 also includes a manifold comprising a plurality of flow hoods, which in this example are depicted at 321, 322, and 323. In this case, each flow hood is disposed on a top surface of a gas sensor that is not visible in this top view (due to each gas sensor being positioned under or beneath each of the flow hoods depicted at 321, 322, and 323).

Figure 4:
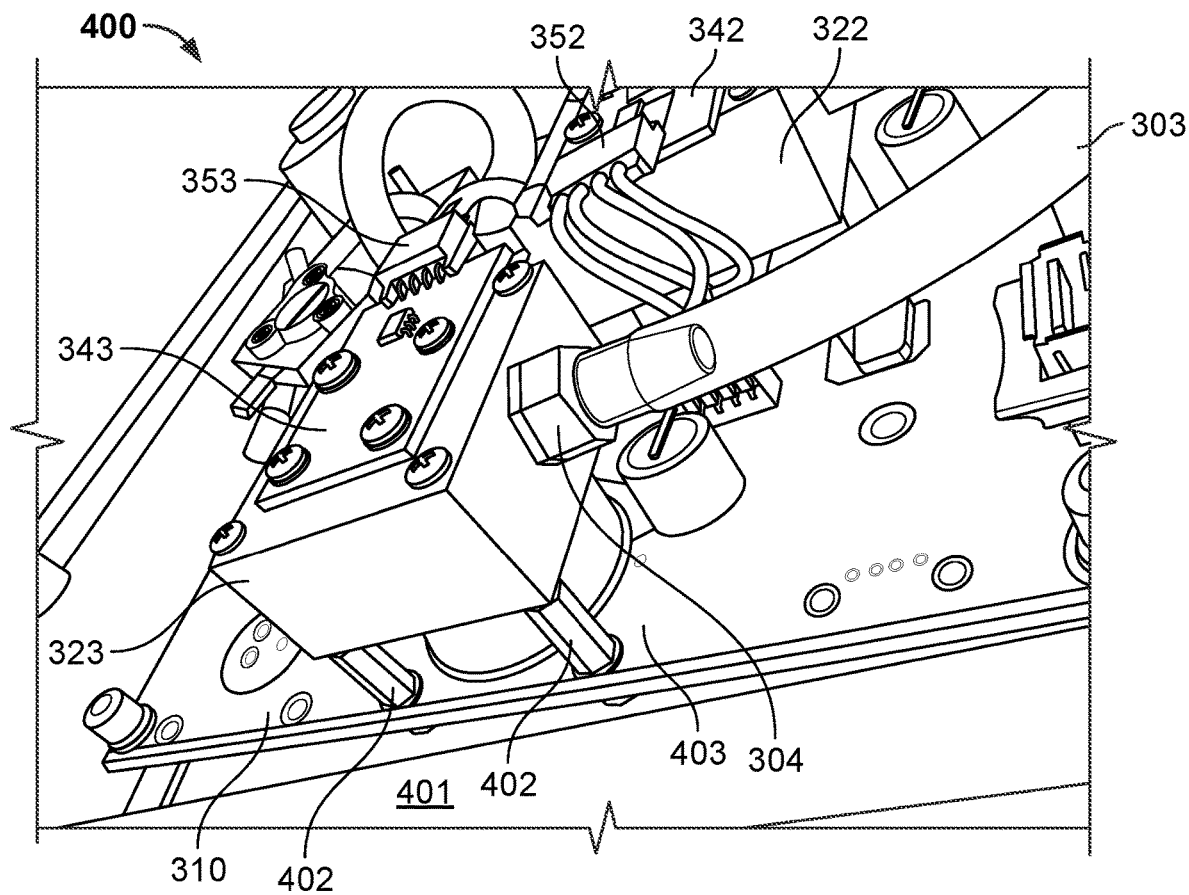
FIG. 4 shows a perspective view of a portion of the exemplary embodiment of the system of FIG. 3 in which a sensor is visible and is shown positioned under a flow hood.

FIG. 4 shows a perspective view 400 of a portion of the exemplary embodiment of the system of FIG. 3 in which a gas sensor is visible and is shown positioned under a flow hood. In the example shown, a gas sensor 401 is coupled to a gas sensor module 403 (shown as an area on the printed circuit board 310). Also shown in FIG. 4 are supports (e.g., depicted at 402) that provide a structure to raise or position a flow hood (e.g., flow hood 323) over a gas sensor (e.g., gas sensor 401). In this case, flow hood 323 is coupled to gas sensor 401 to form a seal such that a fluid flowing through the flow hood at 323 and across a top surface of gas sensor 401 is contained within a controlled and closed volume configured to prevent leakage and contamination of a fluid flowing within the manifold and to prevent exposure of the fluid within the manifold to the environment outside of the manifold. The manifold is thus configured to provide a closed system through which a fluid sample can flow across various gas sensors in a controlled manner that limits exposure of the fluid sample to the outside environment.

Returning to FIG. 3, the top view 300 depicts a first flow hood in the manifold (e.g., flow hood 321) connected to a fluid input source via a fitting at 301. In the example shown, connective tubing (e.g., connective tubing 311) is used to obtain a fluid sample (e.g., an air sample) from the environment being monitored (e.g., a fluid input source). In some cases, the fluid sample comprises an air sample being pumped or pulled into the manifold from the fluid input source in order to be tested or measured by the various sensors that are integrated in the system.

Connective tubing is also used to connect a flow hood to another flow hood or to connect various components to each other in the manifold or on the primary substrate to provide and to actively control a flow of fluid through a sequence or series of interconnected flow hoods and components in the manifold. In this embodiment, a fluid sample is obtained from a fluid input source via connective tubing at 311 and is passed through (pulled or pushed through) flow hood 321. The fluid is received by or enters flow hood 321 via an input port of flow hood 321 (e.g., depicted at 371) and leaves or exits via an output port of flow hood 321 (e.g., depicted at 372). Note that each flow hood is configured to have an input port for receiving a fluid and an output port for releasing a fluid. The flow of fluid through a given flow hood is determined by how each flow hood is connected in a sequence or series of flow hoods that form the manifold and how the fluid is pulled through the manifold.

As shown in FIG. 3, flow hood 321 is connected via connective tubing (e.g., connective tubing 303), which is coupled to flow hood 321 by a fitting (e.g., fitting 302 positioned at output port 372) and to flow hood 323 by a fitting (e.g., fitting 304 at input port 375 of flow hood 323). Accordingly, in the example shown, a fluid sample (e.g., an air sample) that is passed through flow hood 321 (e.g., a fluid sample that is received via input port 371 and released through output port 372) is subsequently passed through flow hood 323 via the connective tubing 303. Although not implemented in the embodiment shown in FIG. 3, connective tubing can also be used to connect flow hood 323 to flow hood 322 (e.g., by coupling connective tubing using fitting 305 on flow hood 323 to fitting 306 on flow hood 322). In the case where connective tubing is used to link or connect flow hood 323 to flow hood 322, the fluid sample would continue to flow from flow hood 323 (e.g., the fluid sample is received via input port 375 and released through output port 376) to flow hood 322.

Continuing with this example, the fluid sample can enter or be received by flow hood 322 at the input port 373 and, after flowing across a top surface of a gas sensor disposed under or beneath flow hood 322, can be released through output port 374. In this case, connective tubing 308 is coupled via fitting 307 to output port 374 of flow hood 322. This connective tubing 308 is also coupled or connected to flow meter 325, forming a connection between flow hood 322 and flow meter 325. After the fluid sample passes through flow hood 322, it is received by flow meter 325 before being passed to a subsequent sensor (depicted at 315) via connective tubing (e.g., depicted at 309).

FIG. 3 depicts an example of a system configured to provide a fluid sample to various gas sensors via a manifold that includes a plurality of flow hoods by actively controlling a flow of fluid (e.g., the fluid sample) through a sequence or series of flow hoods in a selected or particular flow order. As an example, in this case, the fluid sample is obtained from a fluid source and is passed over a sensor (e.g., disposed beneath flow hood 321) that measures or detects a particular gas (e.g., nitrogen dioxide). The fluid sample is then passed to another sensor (e.g., disposed beneath flow hood 323) that measures or detects a particular gas (e.g., nitrogen oxide). The fluid sample can then be passed (e.g., via connective tubing, not shown here) to another sensor (e.g., disposed beneath flow hood 323) in order to measure or detect another gas (e.g., carbon monoxide) and then to a flow meter (e.g., flow meter 325) in order to measure a flow of the fluid sample as it is passing through the manifold. Finally, the fluid sample can be returned from the flow meter to be measured by another sensor, which in this case is depicted as sensor 315 in order to measure or detect a particular gas.

In this manner and as described with respect to FIG. 3, the system is configured to provide active control of a fluid flow in a selected or particular flow order or flow sequence across various types of sensors depending on the application. This provides an advantage of being able to provide the cleanest sample (e.g., a sample with limited exposure to components that might react with the gas to be measured) to selected gas sensors first. For example, in order to obtain a high quality measurement while limiting exposure to components that contribute to contamination in the sample, gas sensors for measuring highly reactive or sensitive gases or for measuring gases present in trace amounts are positioned to receive the fluid sample at an earlier point in the flow order or earlier position in the flow sequence, while gas sensors for less reactive or sensitive gases or gases present in relatively large amounts in the fluid sample are positioned to receive the fluid sample at a later point in the flow order or later position in the flow sequence.

Specifically, in the example described with respect to FIG. 3, a sensor (not shown) for measuring the highly reactive gas $NO_2$ is positioned or disposed beneath flow hood 321 to place the $NO_2$ gas sensor in a position to receive and measure the fluid sample at an earliest point in the flow order. This enables the system to provide as clean of a fluid sample as possible to the $NO_2$ gas sensor by limiting the exposure of the sample to materials and components that react with $NO_2$ gas, resulting in a more accurate measurement. Similarly, because NO is also highly reactive, although perhaps less reactive than $NO_2$, a sensor (not shown) for measuring the highly reactive gas NO is positioned or disposed beneath flow hood 323, which places the NO gas sensor in a position to receive and measure the fluid sample at a relatively early point in the flow order. In contrast, a sensor 315 for measuring $CO_2$ gas (which is much less reactive than $NO_2$ or NO) is positioned to receive and measure the fluid sample at a later point in the flow order. In this case, the fluid sample reaches the $CO_2$ gas sensor (e.g., sensor 315) after having passed through sensors disposed beneath several flow hoods (e.g., flow hood 321, flow hood 323, and flow hood 322), wherein each flow hood is configured to be disposed on a top surface of a gas sensor for measuring a particular gas, and after having passed through a flow meter (e.g., flow meter 325). Thus, as described in this example, certain sensors can be selected to be positioned to receive the fluid sample in a particular flow order depending on the application and the particular characteristics of the pollutants desired to be measured.

In some cases, the system further includes a plurality of secondary substrates, wherein each secondary substrate is disposed on a top surface of a flow hood in the manifold. In the example shown in FIG. 3, each of the secondary substrates (e.g., secondary substrate 341, secondary substrate 342, and secondary substrate 343) is a printed circuit board configured to measure a set of environmental metrics, which in this case includes temperature, pressure, and humidity. In this configuration, measurements of temperature, pressure, and humidity at sensor points corresponding to locations of the gas sensors positioned beneath each of the flow hoods on which a secondary substrate is disposed are obtained. Here, secondary substrate 341 is configured to obtain measurements of temperature, pressure, and humidity at a sensor point corresponding to a location of a gas sensor positioned beneath flow hood 321; secondary substrate 342 is configured to obtain measurements of temperature, pressure, and humidity at a sensor point corresponding to a location of a gas sensor positioned beneath flow hood 322; and secondary substrate 343 is configured to obtain measurements of temperature, pressure, and humidity at a sensor point corresponding to a location of a gas sensor positioned beneath flow hood 323.

Figure 5A:
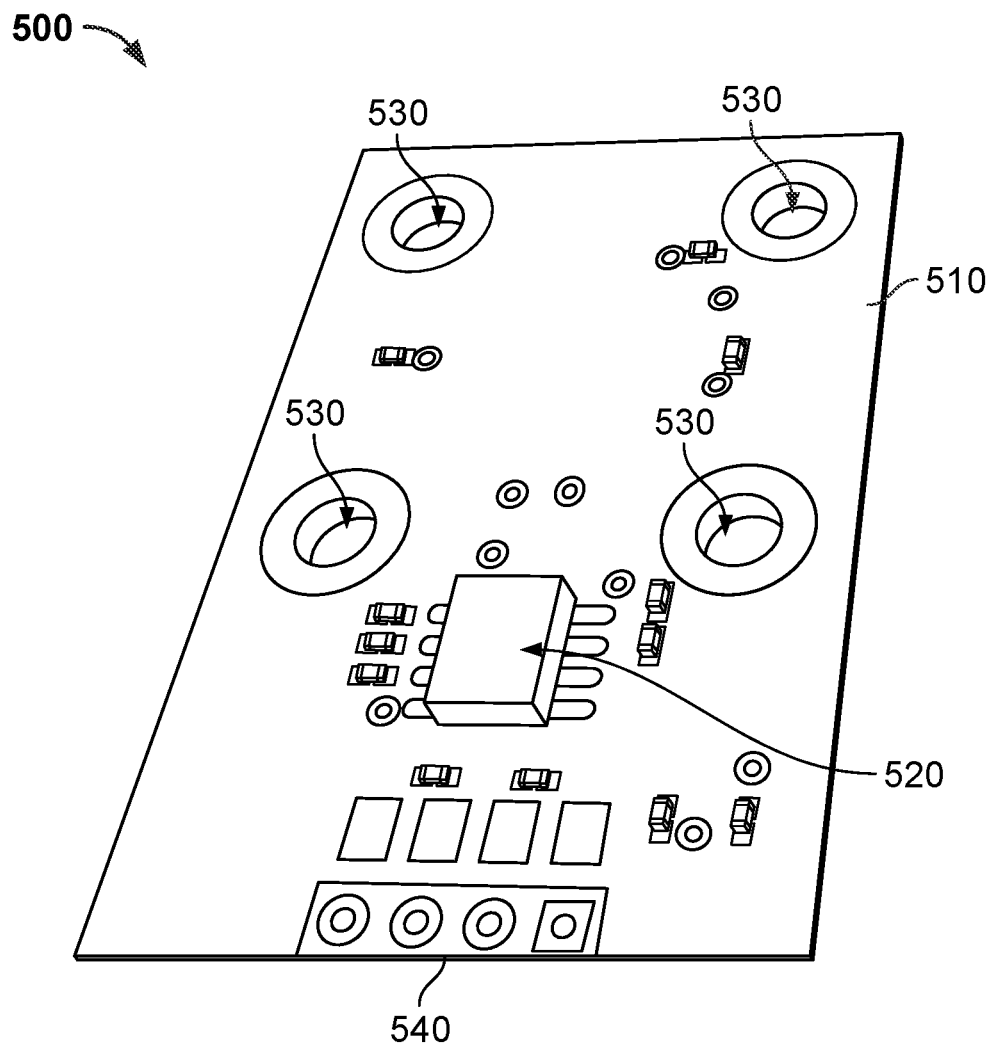
FIG. 5A shows a top view of an embodiment of a secondary substrate included in some embodiments of the system as disclosed herein.

FIG. 5A shows a top view 500 of an embodiment of a secondary substrate (e.g., secondary substrate 341, secondary substrate 342, and secondary substrate 343) included in some embodiments of the system as disclosed herein. In the example shown, the secondary substrate comprises a printed circuit board, a top surface of which is depicted at 510. Disposed on the top surface of the secondary substrate is a unique ID chip 520, a set of mounting holes 530, and a power and data interface 540. The unique ID chip 520 serves to provide a unique identifier for the secondary substrate, which can be used in identifying data or measurements obtained by the secondary substrate (e.g., environmental metrics including temperature, pressure and humidity) that are sent to a data processor for analysis.

In the embodiment of FIG. 5A, the set of mounting holes 530 are used to mount the secondary substrate to a top surface of a flow hood as described above. Note however that other means of coupling the secondary substrate to the top surface of a flow hood may be used without limiting the scope of the system as described herein. The power and data interface 540 is used to provide an ability to connect the secondary substrate to a power source (not shown) and data processor (not shown) that processes data or measurements obtained by components disposed on the secondary substrate.

Figure 5B:
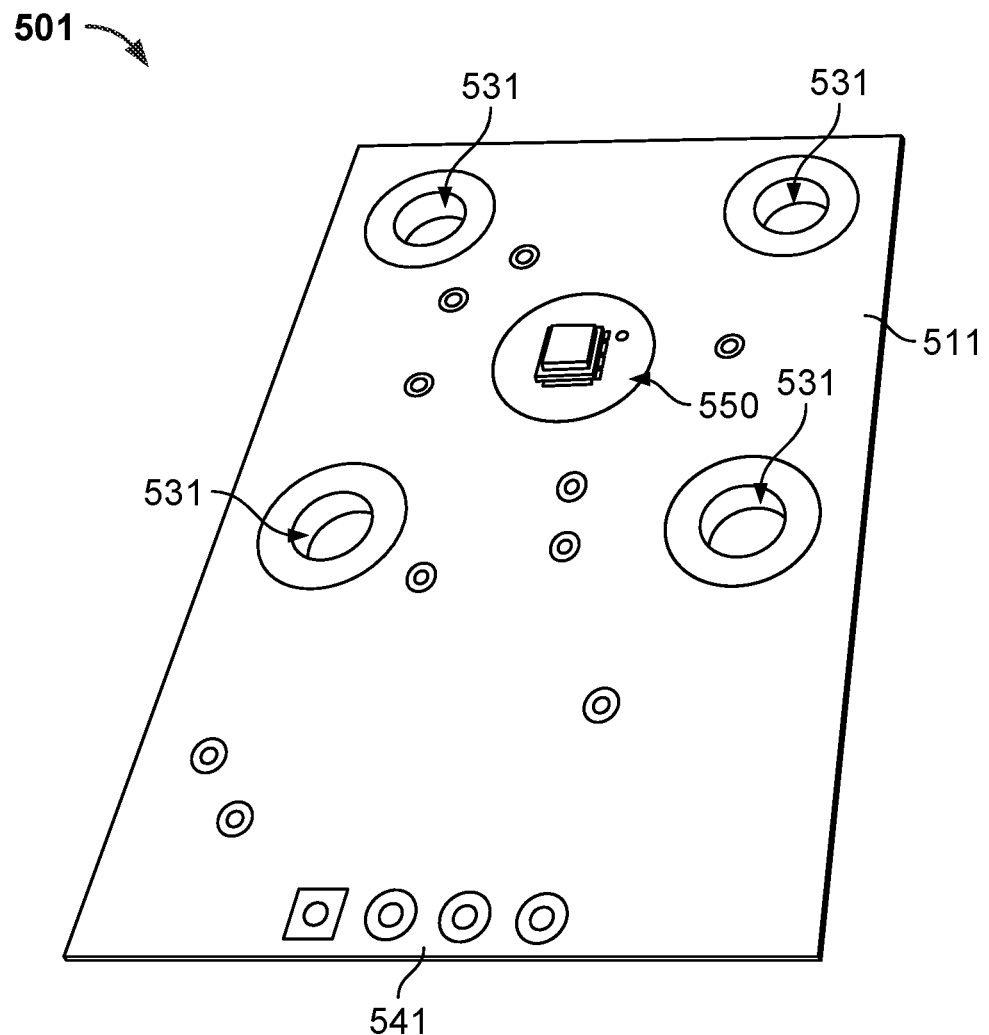
FIG. 5B shows a bottom view of an embodiment of the secondary substrate shown in FIG. 5A.

FIG. 5B shows a bottom view 501 of an embodiment of the secondary substrate (e.g., secondary substrate 341, secondary substrate 342, and secondary substrate 343) shown in FIG. 5A. As described above, the secondary substrate comprises a printed circuit board, a bottom surface of which is depicted at 511. Disposed on a bottom surface 511 of the secondary substrate is a sensor 550, a view of the bottom of a set of mounting holes shown at 531, and a view of the bottom of a power and data interface shown at 541. In this case, the sensor is configured to obtain environmental metrics that include temperature, pressure and humidity.

Returning to FIGS. 3 and 4, note that in the example depicted, a set of connectors (e.g., connector 351, connector 352, and connector 353) are shown. In this example, each connector is configured to couple to the power and data interface (e.g., power and data interface 540 of FIG. 5A) of each of the secondary substrates (e.g., secondary substrate 341, secondary substrate 342, and secondary substrate 343) in order to provide a connection to a power source (not shown) and to a data processor (not shown).

In some embodiments, each connector (e.g., connector 351, connector 352, and connector 353) is configured to couple a device to the primary substrate or to provide a connection from a sensor module to a data processor. In some cases, the data processor is a component of the system.

Additionally, in the example shown, data connectors (e.g., USB connectors depicted at 361 and 362) and Ethernet connectors (e.g., depicted at 363) provide an ability to make a data connection to a data processor (not shown) or to a sensor (e.g., a particulate matter sensor). The data processor is configured to receive and process data obtained from various gas sensors and other devices coupled (e.g., electrically or mechanically) to the primary substrate. In this manner, the system is configured to electrically couple and provide data connections to various devices (e.g., USB or Ethernet devices) even if such devices are not mechanically disposed on or physically mounted or coupled directly to the primary substrate.

Figure 6:
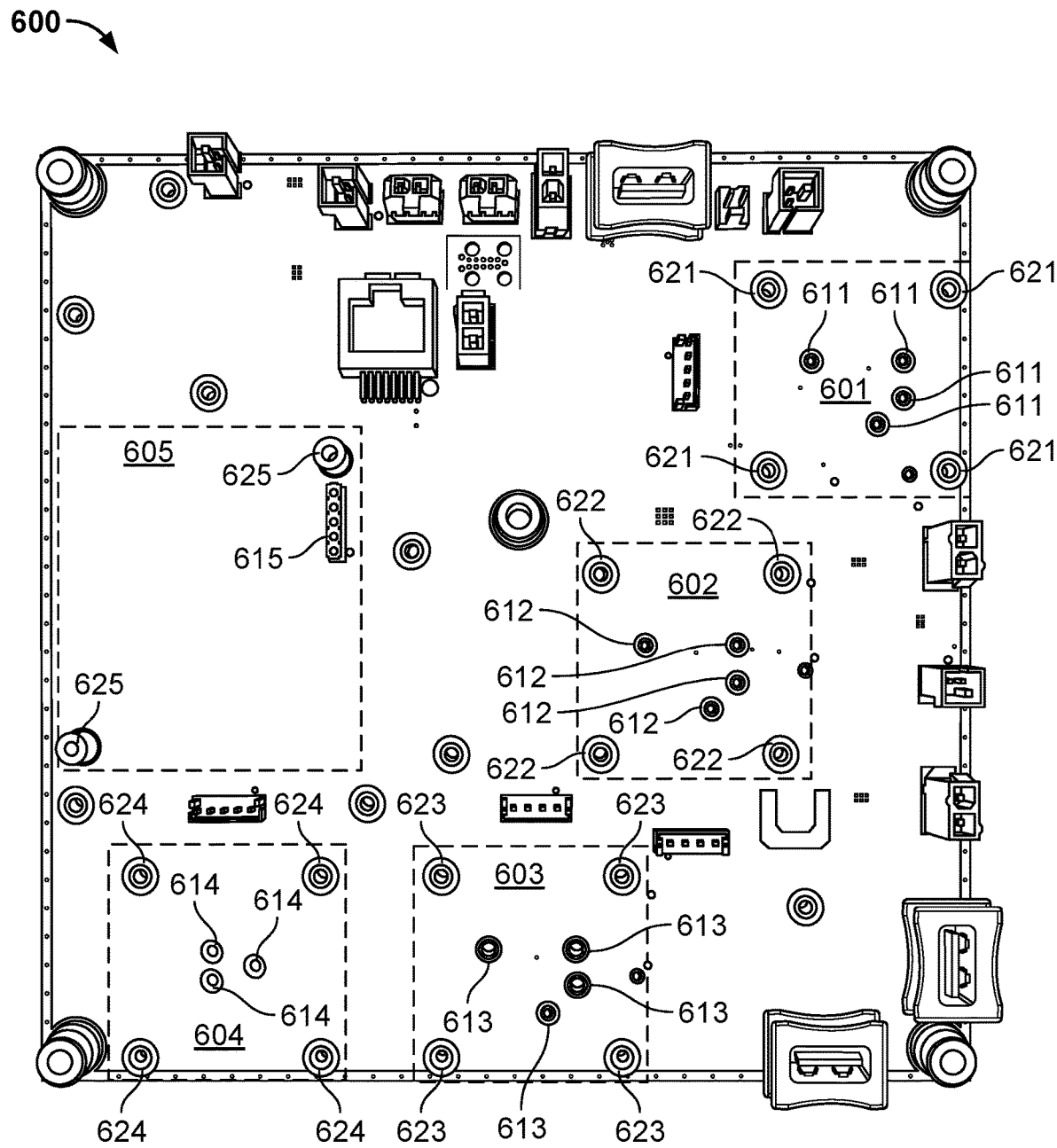
FIG. 6 shows an exemplary embodiment of a primary substrate as disclosed herein that includes a plurality of sensor modules.

FIG. 6 shows an exemplary embodiment of a primary substrate as disclosed herein that includes a plurality of sensor modules. In this case, the plurality of sensor modules includes sensor modules depicted at 601, 602, 603, 604, and 605. Each sensor module in the plurality of sensor modules is configured to couple to a sensor. In some cases, as described in further detail below, each sensor module is configured to mechanically and electrically couple to a particular sensor.

In the example shown, sensor module 601 includes a plurality of receptacles (shown at 611) configured to couple to electrodes of a gas sensor (e.g., gas sensors shown at 111 of FIG. 1 and at 211 of FIG. 2) such as for example, a sensor for measuring $NO_2$. Additionally, sensor module 601 also includes a plurality of threaded mounting holes (shown at 621) configured to couple to fasteners of a flow hood (e.g., shown at 121 of FIG. 1 and 221 of FIG. 2).

Sensor module 602 includes a plurality of receptacles (shown at 612) configured to couple to electrodes of a gas sensor (e.g., gas sensors shown at 112 of FIG. 1 and at 212 of FIG. 2) such as for example, a sensor for measuring CO. Sensor module 602 also includes a plurality of threaded mounting holes (shown at 622) configured to couple to fasteners of a flow hood (e.g., shown at 122 of FIG. 1 and 222 of FIG. 2).

Sensor module 603 includes a plurality of receptacles (shown at 613) configured to couple to electrodes of a gas sensor (e.g., gas sensors shown at 113 of FIG. 1 and at 213 of FIG. 2) such as for example, a sensor for measuring NO. Sensor module 603 also includes a plurality of threaded mounting holes (shown at 623) configured to couple to fasteners of a flow hood (e.g., shown at 123 of FIG. 1 and 223 of FIG. 2).

Sensor module 604 includes a plurality of receptacles (shown at 614) configured to couple to electrodes of a gas sensor (e.g., gas sensors shown at 114 of FIG. 1 and at 214 of FIG. 2) such as for example, a sensor configured to detect or measure volatile organic compounds (VOC). Sensor module 604 also includes a plurality of threaded mounting holes (shown at 624) configured to couple to fasteners of a flow hood (e.g., shown at 124 of FIG. 1 and 224 of FIG. 2).

Sensor module 605 includes a power and data connector (shown at 615) and a plurality of threaded mounting holes (shown at 625) configured to couple to or connect with a gas sensor (e.g., gas sensors shown at 115 of FIG. 1 and at 215 of FIG. 2) such as for example, a sensor for measuring $CO_2$.

In some embodiments, the disclosed system is used to perform a method for monitoring and collecting environmental data that supports the acquisition of quality measurements of contaminants or pollutants by sensors based on different technologies in an integrated manner. Embodiments of various methods performed by the disclosed system are described with respect to the following figures.

Figure 7:
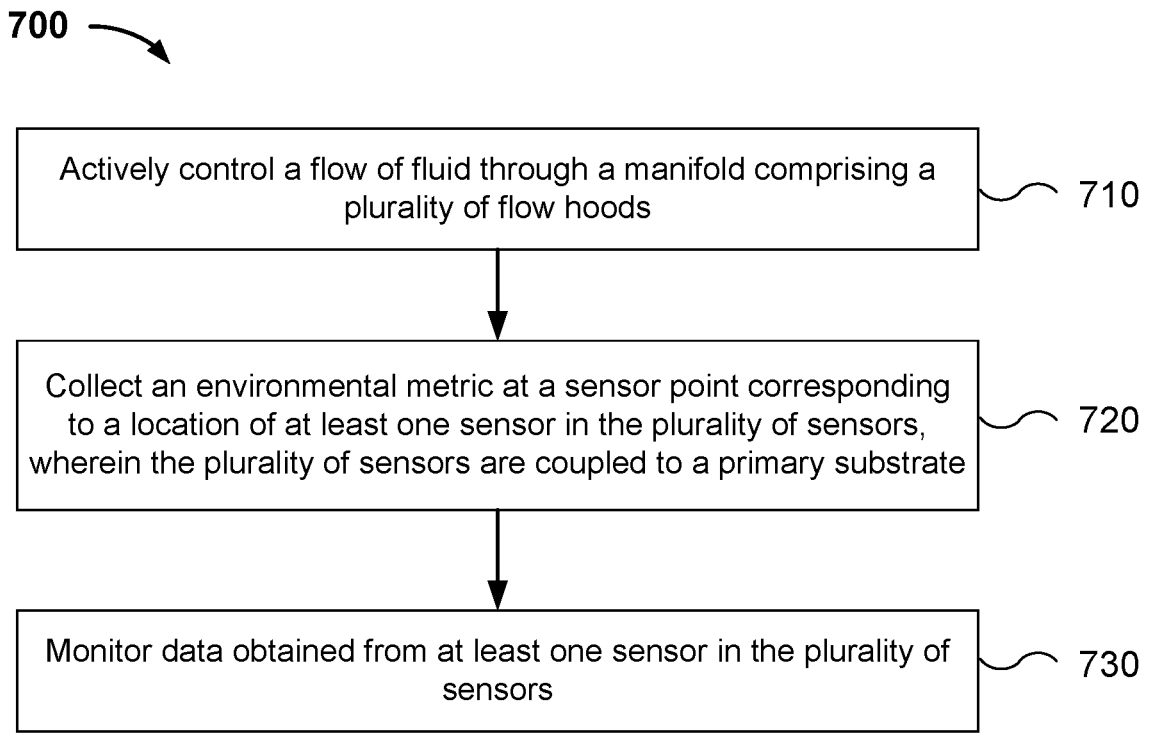
FIG. 7 is a flow chart depicting a method for monitoring and collecting environmental data that can be performed by the system as disclosed herein.

FIG. 7 is a flow chart depicting a method 700 for monitoring and collecting environmental data that can be performed by the system as disclosed herein. Referring to FIG. 7, the method 700 includes at 710, actively controlling a flow of fluid through a manifold comprising a plurality of flow hoods (e.g., depicted at 121, 122, 123 and 124 in FIG. 1 and at 221, 222, 223, and 224 in FIG. 2). In some embodiments, at least one flow hood in the plurality of flow hoods is disposed on a top surface of at least one sensor in the plurality of sensors (e.g., depicted at 111, 112, 113, 114, and 115 in FIG. 1 and at 211, 212, 213, 214, and 215 in FIG. 2) disposed on the primary substrate. In some cases, at least one sensor in the plurality of sensors is coupled to a sensor module (e.g., sensor modules depicted at 101-105 in FIG. 1 or sensor modules depicted at 201-205 in FIG. 2) on the primary substrate. Additionally, as shown in FIGS. 3 and 4, a flow hood in the manifold is connected to another component in the manifold or on the primary substrate (e.g., via connective tubing as depicted at 303 in FIGS. 3 and 4). Note that in some embodiments, connective tubing is also used to connect a component (e.g., a flow meter) to another component (e.g., a flow hood disposed on a top surface of a sensor), as shown for example in the connective tubing depicted at 308 and 309 in FIG. 3.

At 720, the method 700 includes collecting an environmental metric at a sensor point corresponding to a location of at least one sensor in the plurality of sensors, wherein the plurality of sensors are coupled to a primary substrate. In some embodiments, the primary substrate (e.g., primary substrate 110 of FIG. 1 or primary substrate 210 of FIG. 2) includes a plurality of sensor modules (e.g., sensor modules depicted at 101-105 in FIG. 1 or sensor modules depicted at 201-205 in FIG. 2). In some embodiments, each sensor module is configured to couple to or engage with a sensor and the method includes coupling a particular sensor to a particular sensor module on the primary substrate. In some cases, each sensor module is configured to mechanically and electrically couple to or engage with a sensor. For example, each sensor module includes an area (e.g., a recessed area or slot) configured to engage or to couple with a particular sensor (e.g., by mounting or inserting the sensor on or into a recessed area or slot) in the plurality of sensors.

In some embodiments, a secondary substrate (e.g., depicted in FIGS. 5A-5B) is used for collecting one or more environmental metrics. In some cases, a plurality of secondary substrates is used (see, e.g., FIG. 1 at 141, 142, 143, and 144; FIG. 2 at 241, 242, 243, and 244; FIG. 3 at 341, 342, and 343), wherein each secondary substrate in the plurality of secondary substrates is disposed on a top surface of a flow hood in the manifold, as shown in the embodiments of FIGS. 1, 2, 3 and 4. In some instances, a secondary substrate on a given flow hood is configured to capture an environmental metric at a sensor point corresponding to a location of a sensor on which the given flow hood is disposed.

At 730, the method 700 includes monitoring data obtained from at least one sensor in the plurality of sensors using a data processor. In particular, as shown in FIG. 1, the primary substrate includes a connector configured to provide a connection from a sensor module to a data processor, the data processor being configured to monitor sensor data received from a sensor coupled to the sensor module. As described above, in some embodiments a sensor module is configured to mechanically and electrically couple to a sensor. In the examples shown, one or more data connectors (e.g., USB connectors depicted at 151, 152, and 153 and Ethernet connector at 154 in FIG. 1) provide an ability to make or establish a connection between a data processor and a sensor. The data processor is configured to receive and process data obtained from various sensors and other devices coupled (e.g., electrically or mechanically) to the primary substrate. In some embodiments and as described with respect to the following figures, gas sensors are used to detect and measure pollutants or contaminants.

Figure 8:
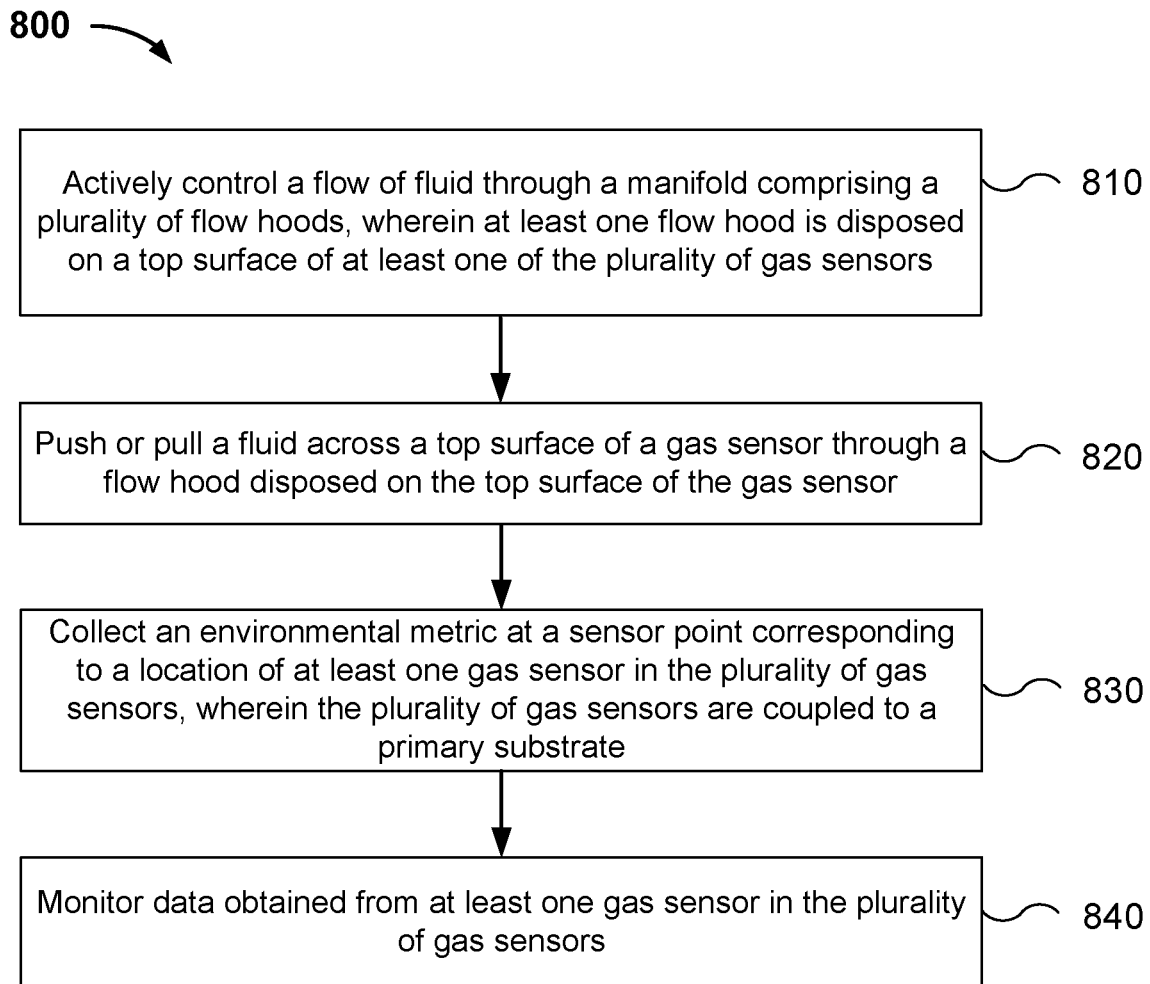
FIG. 8 is a flow chart depicting a method for monitoring and collecting environmental data that includes the use of gas sensors to detect and measure pollutants in the air.

FIG. 8 is a flow chart depicting a method 800 for monitoring and collecting environmental data that includes the use of gas sensors to detect and measure pollutants in the air. Referring to FIG. 8, the method 800 includes at 810, actively controlling a flow of fluid through a manifold comprising a plurality of flow hoods. In some embodiments, at least one flow hood in the plurality of flow hoods is disposed on a top surface of at least one gas sensor in the plurality of gas sensors. In some cases, at least one gas sensor in the plurality of gas sensors is coupled to a gas sensor module on the primary substrate. Additionally, as shown in FIGS. 3 and 4, a flow hood in the manifold is connected to another component in the manifold or on the primary substrate. Note that in some embodiments, connective tubing is also used to connect a component to another component, as shown for example in the connective tubing depicted at 308 and 309 in FIG. 3.

At 820, the method 800 includes pushing or pulling a fluid across a top surface of a gas sensor through a flow hood disposed on the top surface of the gas sensor. In particular, the manifold is configured to enable active and independent control of a fluid flow (e.g., an air sample) over at least one of the gas sensors disposed on the primary substrate by providing a closed system through which a fluid sample can flow across various gas sensors in a controlled manner through a series of flow hoods that limit exposure to the outside environment. The fluid enters each flow hood through an input port and leaves each fluid port through an output port. A fitting is used at the input and output ports to attach or couple connective tubing that accommodates a flow of the fluid through the manifold. The manifold is configured to provide active flow control of a fluid flow by pushing or pulling a fluid across a top surface of a gas sensor through a flow hood disposed on the top surface of the gas sensor. In the case where a plurality of gas sensors are used, the manifold is configured to provide active flow control of a plurality of fluid flows by pushing or pulling a fluid across a top surface of each of a plurality of gas sensors through a flow hood disposed on the top surface of each of the plurality of gas sensors.

At 830, the method 800 includes collecting an environmental metric at a sensor point corresponding to a location of at least one gas sensor in the plurality of gas sensors, wherein the plurality of gas sensors are coupled to a primary substrate. In some embodiments, the primary substrate (e.g., primary substrate 110 of FIG. 1 or primary substrate 210 of FIG. 2) includes a plurality of gas sensor modules. In some embodiments, each gas sensor module is configured to couple to or engage with a gas sensor and the method includes coupling a particular gas sensor to a particular gas sensor module on the primary substrate. In some cases, each gas sensor module is configured to mechanically and electrically couple to or engage with a gas sensor. For example, each gas sensor module includes an area (e.g., a recessed area or slot) configured to engage or to couple with a particular gas sensor (e.g., by mounting or inserting the sensor on or into a recessed area or slot) in the plurality of gas sensors.

In some embodiments, a secondary substrate (e.g., depicted in FIGS. 5A-5B) is used for collecting one or more environmental metrics. In some cases, a plurality of secondary substrates is used, wherein each secondary substrate in the plurality of secondary substrates is disposed on a top surface of a flow hood in the manifold, as shown in the embodiments of FIGS. 1, 2, 3 and 4. In some instances, a secondary substrate on a given flow hood is configured to capture an environmental metric at a sensor point corresponding to a location of a gas sensor on which the given flow hood is disposed.

At 840, the method 800 includes monitoring data obtained from at least one gas sensor in the plurality of gas sensors using a data processor. In particular, as shown in FIG. 1, the primary substrate includes a connector configured to provide a connection from a gas sensor module to a data processor, the data processor being configured to monitor gas sensor data received from a gas sensor coupled to the gas sensor module. As described above, in some embodiments a gas sensor module is configured to mechanically and electrically couple to a gas sensor. In the examples shown, one or more data connectors provide an ability to make or establish a connection between a data processor and a gas sensor. The data processor is configured to receive and process data obtained from various gas sensors and other devices coupled (e.g., electrically or mechanically) to the primary substrate.

Figure 9:
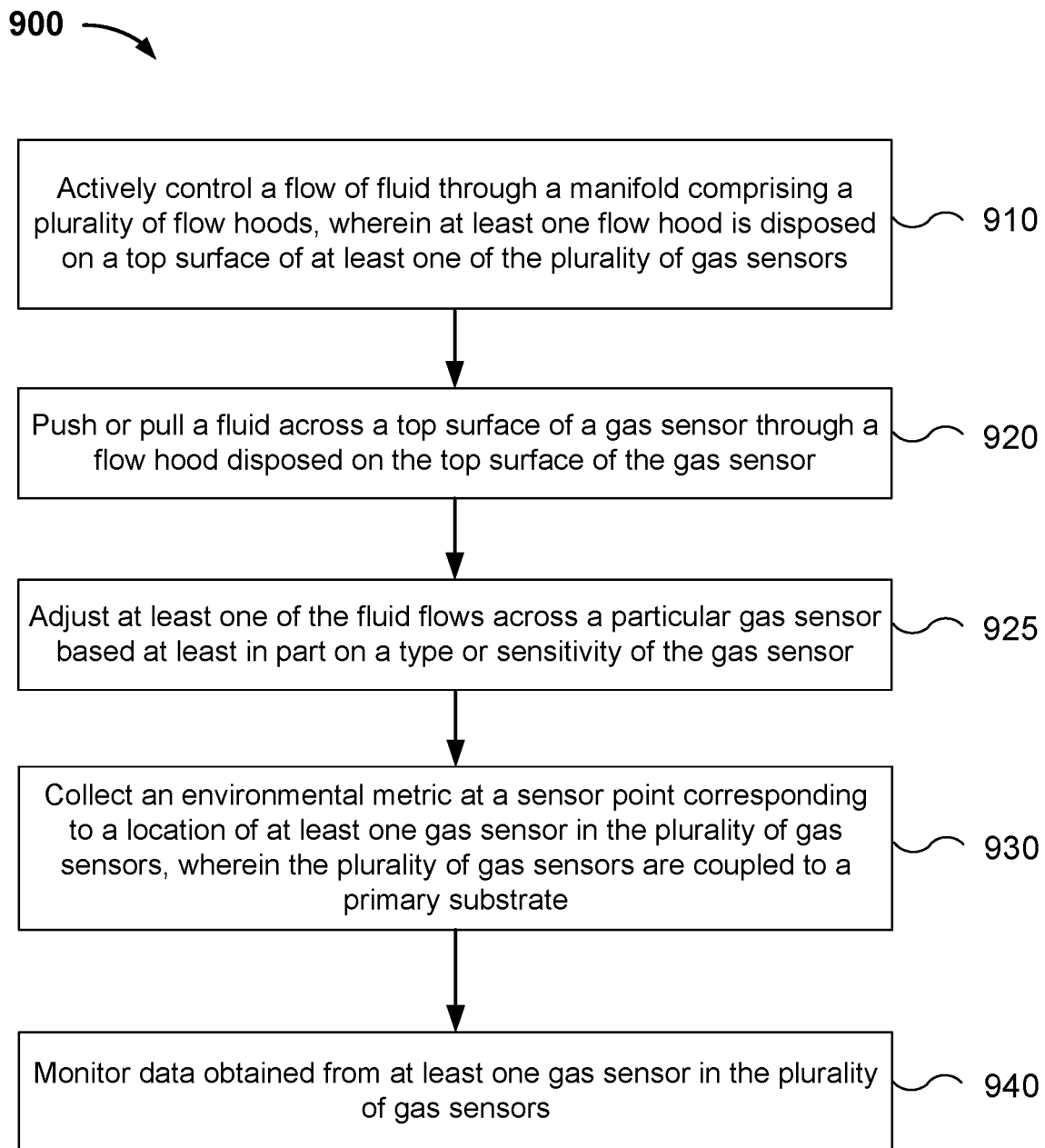
FIG. 9 is a flow chart depicting a method for monitoring and collecting environmental data that includes a step of adjusting at least one of the fluid flows across a particular gas sensor based at least in part on a type or sensitivity of the gas sensor.

FIG. 9 is a flow chart depicting a method 900 for monitoring and collecting environmental data that includes a step of adjusting at least one of the fluid flows across a particular gas sensor based at least in part on a type or sensitivity of the gas sensor.

Referring to FIG. 9, the method 900 includes certain steps described above with respect to method 800 of FIG. 8. Specifically, method 900 includes: actively controlling a flow of fluid through a manifold comprising a plurality of flow hoods at 910, wherein at least one flow hood in the plurality of flow hoods is disposed on a top surface of at least one gas sensor in the plurality of gas sensors and pushing or pulling a fluid across a top surface of a gas sensor through a flow hood disposed on the top surface of the gas sensor at 920. But in the example shown, method 900 includes an additional step at 925 of adjusting at least one of the fluid flows across a particular gas sensor based at least in part on a type or sensitivity of the gas sensor. FIG. 9 also shows that method 900 includes collecting an environmental metric at a sensor point corresponding to a location of at least one gas sensor in the plurality of gas sensors at 930, wherein the plurality of gas sensors are coupled to a primary substrate. Finally, the method 900 includes monitoring data obtained from at least one gas sensor in the plurality of gas sensors using a data processor at 940.

In some embodiments, the method includes using a pump system to actively control a fluid flow through the manifold and across the face or top surface of each gas sensor. In particular, the pump system is configured to independently either pull or push a fluid sample across the face or top surface of a given gas sensor through a flow hood disposed on the top surface of the given gas sensor. In some instances, the pump system includes a plurality of pump units, each pump unit having a vacuum side and a pressure side to either pull or push a fluid across a top surface of a gas sensor. For example, to pull a fluid flow across a top surface of a given gas sensor, a pump unit is positioned on a backside of the sensor to draw air towards the sensor from the backside of the sensor. Alternately, to push a fluid flow across a top surface of a given gas sensor, a pump unit is positioned on a front side of the given gas sensor to push or blow air through the manifold towards the gas sensor.

By using the pump system to pull or push a fluid through a flow hood in the manifold, the manner of providing a fluid sample to a particular gas sensor can be adjusted (e.g., as depicted at step 925 of method 900 of FIG. 9) based on a type or sensitivity of the particular gas sensor (e.g., the reactivity of the gas being measured by the given gas sensor or the optimal environmental conditions for the operation of a particular sensor). For example, in the case of a sensor for measuring a highly reactive and unstable pollutant, pushing an air sample will cause at least some of the highly reactive and unstable pollutant in the air sample to be lost. Accordingly, in this case, a pump unit is configured to pull air towards the sensor for measuring the highly reactive and unstable pollutant, providing the air sample to the sensor before it is exposed to any other components (e.g., pump units or mechanical structures) that might compromise the air sample. In contrast, for a less reactive and much more stable pollutant, the pump unit is configured to push air towards the sensor for measuring the less reactive pollutant.

Figure 10:
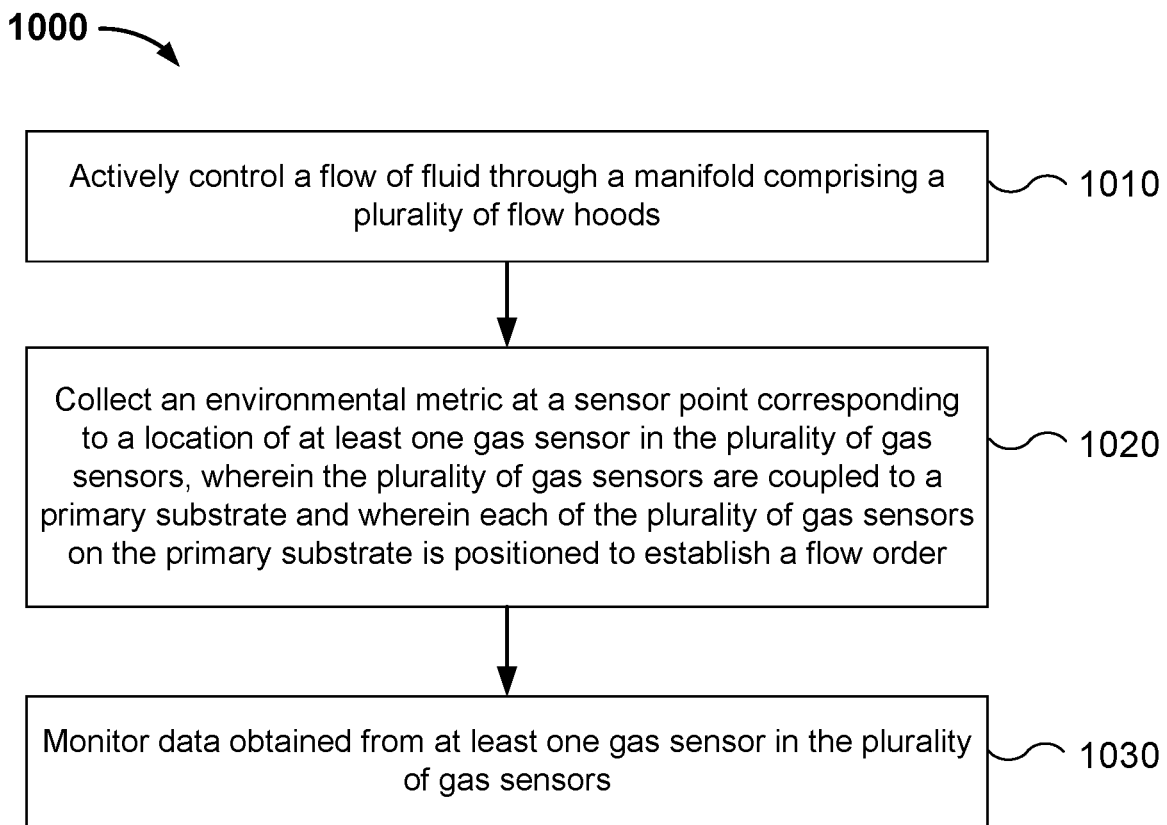
FIG. 10 is a flow chart depicting a method for monitoring and collecting environmental data, wherein each of a plurality of gas sensors on a primary substrate is positioned to establish a flow order.

FIG. 10 is a flow chart depicting a method 1000 for monitoring and collecting environmental data wherein each of a plurality of gas sensors on a primary substrate is positioned to establish a flow order.

Specifically, referring to FIG. 10, the method 1000 includes actively controlling a flow of fluid through a manifold comprising a plurality of flow hoods at 1010. In some embodiments, at least one flow hood in the plurality of flow hoods is disposed on a top surface of at least one gas sensor in a plurality of gas sensors. In some cases, at least one gas sensor in the plurality of gas sensors is coupled to a gas sensor module on the primary substrate. The primary substrate includes a plurality of gas sensor modules, each gas sensor module being configured to couple to or engage with a gas sensor. In some embodiments, each gas sensor module is configured to couple to or engage with a gas sensor and the method includes coupling a particular gas sensor to a particular gas sensor module on the primary substrate. In some cases, each gas sensor module is configured to mechanically and electrically couple to or engage with a gas sensor.

Additionally, as shown in FIGS. 3 and 4, a flow hood in the manifold is connected to another component in the manifold or on the primary substrate. Note that in some embodiments, connective tubing is also used to connect a component to another component, as shown for example in the connective tubing depicted at 308 and 309 in FIG. 3.

At 1020, the method 1000 includes collecting an environmental metric at a sensor point corresponding to a location of at least one gas sensor in the plurality of gas sensors, wherein the plurality of gas sensors are coupled to a primary substrate and wherein each of the plurality of gas sensors on the primary substrate is positioned to establish a flow order. In some embodiments, the primary substrate (e.g., primary substrate 110 of FIG. 1 or primary substrate 210 of FIG. 2) includes a plurality of gas sensor modules. In some embodiments, each gas sensor module is configured to couple to or engage with a gas sensor and the method includes coupling a particular gas sensor to a particular gas sensor module on the primary substrate. In some cases, each gas sensor module is configured to mechanically and electrically couple to or engage with a gas sensor. For example, each gas sensor module includes an area (e.g., a recessed area or slot) configured to engage or to couple with a particular gas sensor (e.g., by mounting or inserting the sensor on or into a recessed area or slot) in the plurality of gas sensors.

In some embodiments, each of the plurality of gas sensors is positioned on the primary substrate to establish an order of fluid flows across a top surface of each gas sensor in the plurality of gas sensors based at least in part on a type or a sensitivity of each gas sensor. The order of fluid flows across a top surface of each gas sensor in a series of gas sensors sets or establishes a flow order or flow sequence. For example, to obtain a high quality measurement while limiting exposure to components that contribute to contamination in the sample, gas sensors for measuring highly reactive or sensitive gases or for measuring gases present in trace amounts are positioned to receive the fluid sample at an earlier point in the flow order or earlier position in the flow sequence, while gas sensors for less reactive or sensitive gases or gases present in relatively large amounts in the fluid sample are positioned to receive the fluid sample at a later point in the flow order or later position in the flow sequence.

In some embodiments, a secondary substrate (e.g., depicted in FIGS. 5A-5B) is used for collecting one or more environmental metrics. In some cases, a plurality of secondary substrates is used, wherein each secondary substrate in the plurality of secondary substrates is disposed on a top surface of a flow hood in the manifold, as shown in the embodiments of FIGS. 1, 2, 3 and 4. In some instances, a secondary substrate on a given flow hood is configured to capture an environmental metric at a sensor point corresponding to a location of a gas sensor on which the given flow hood is disposed.

At 1030, the method 1000 includes monitoring data obtained from at least one gas sensor in the plurality of gas sensors using a data processor. In particular, as shown in FIG. 1, the primary substrate includes a connector configured to provide a connection from a gas sensor module to a data processor, the data processor being configured to monitor gas sensor data received from a gas sensor coupled to the gas sensor module. As described above, in some embodiments a gas sensor module is configured to mechanically and electrically couple to a gas sensor. In the examples shown, one or more data connectors provide an ability to make or establish a connection between a data processor and a gas sensor. The data processor is configured to receive and process data obtained from various gas sensors and other devices coupled (e.g., electrically or mechanically) to the primary substrate. Finally, in some cases, the primary substrate includes a connector and the method further comprises coupling a device to the primary substrate using the connector.

In summary, a method and system for monitoring and collecting environmental data are described herein that support acquisition and analysis of quality measurements of pollutants by sensors based on different technologies in an integrated manner. Embodiments of the disclosed system include a primary substrate having a plurality of sensor modules, each sensor module configured to couple to a sensor, and a manifold having a plurality of flow hoods, each flow hood disposed on a top surface of a sensor and connected to another flow hood or another component in the manifold or on the primary substrate.

In some cases, the sensor modules are gas sensor modules, and the sensor is a gas sensor. In these cases, the manifold provides a closed system through which a fluid sample can flow across a series of gas sensors in an actively controlled manner that enables independent flow control over each individual gas sensor while limiting exposure of the fluid sample to potential sources of contamination.

Additionally, using a plurality of secondary substrates, each secondary substrate being disposed on a top surface of a flow hood in the manifold, the system can capture or collect an environmental metric (e.g., pressure, temperature, and humidity) at a sensor point corresponding to a location of the sensor on which the given flow hood is disposed thereby providing a more accurate measurement of the environmental metric.

The system is flexible and through the use of a device connector, can support and integrate devices regardless of whether the devices are physically disposed on or mounted to the primary substrate. The system thus provides electrical support, data support, and mechanical support on a central unit that allows integration of different sensors with different options to obtain and send sensor data for processing and analysis.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for monitoring and collecting environmental data, comprising:
 a primary substrate comprising a plurality of sensor modules, wherein each sensor module is configured to couple to a sensor;
 a manifold comprising a plurality of flow hoods, wherein each flow hood is configured to be disposed on a top surface of a sensor coupled to a sensor module on the primary substrate and wherein a flow hood in the manifold is configured to be connected to another component in the manifold or on the primary substrate such that fluid flows through the plurality of flow hoods in an order based on a sensitivity of the sensor in each of the plurality of sensor modules;
 a plurality of secondary substrates, wherein each secondary substrate is disposed on a top surface of the flow hood in the manifold; and
 a connector disposed on the primary substrate configured to provide a connection from a sensor module to a data processor.

2. The system of claim 1, wherein the sensor modules are gas sensor modules and the sensor is a gas sensor and wherein the manifold is configured to provide active flow control of a fluid flow by pushing or pulling a fluid across a top surface of the gas sensor through the flow hood disposed on the top surface of the gas sensor.

3. The system of claim 1, wherein the sensor modules are gas sensor modules and the sensor is a gas sensor and wherein the manifold is configured to provide active flow control of a plurality of fluid flows by pushing or pulling a fluid across a top surface of each of a plurality of gas sensors through the flow hood disposed on the top surface of each of the plurality of gas sensors, and wherein each of the fluid flows across a given gas sensor can be adjusted based at least in part on a type or the sensitivity of the given gas sensor.

4. The system of claim 1, wherein the sensor modules are gas sensor modules and the sensor is a gas sensor and further comprising a pump system, wherein the pump system is configured to push or pull a fluid across a top surface of a gas sensor through the flow hood disposed on the top surface of the gas sensor.

5. The system of claim 1, wherein the sensor modules are gas sensor modules and the sensor is a gas sensor and further comprising a pump system, wherein the pump system is configured to push or pull a fluid across a top surface of the gas sensor through the flow hood disposed on the top surface of the gas sensor, wherein the pushing or pulling of the fluid is based at least in part on a type or the sensitivity of the gas sensor over which the fluid is flowing and wherein each of the plurality of gas sensor modules is positioned on the primary substrate to establish the order of fluid flow across a top surface of a plurality of gas sensors based at least in part on a type or the sensitivity of a gas sensor.

6. The system of claim 1, wherein the sensor modules are gas sensor modules and the sensor is a gas sensor and wherein each secondary substrate on a given flow hood is configured to capture an environmental metric at a sensor point corresponding to a location of the gas sensor on which the given flow hood is disposed.

7. The system of claim 6, wherein the environmental metric comprises one or more metrics selected from a group consisting of pressure, temperature, and humidity.

8. The system of claim 1, further comprising a device connector configured to couple a device to the primary substrate.

9. A method for monitoring and collecting environmental data, comprising:
 actively controlling a flow of fluid through a manifold comprising a plurality of flow hoods;
 collecting an environmental metric at a sensor point corresponding to a location of at least one sensor in a plurality of sensors, wherein the plurality of sensors is coupled to a primary substrate; and
 monitoring data obtained from at least one sensor in the plurality of sensors using a data processor;
 wherein each of the at least one sensor is positioned to establish an order of the flow of fluid across a surface of each of the plurality of sensors based at least in part on at least one sensitivity of the at least one sensor of the plurality of sensors.

10. The method of claim 9, wherein each of the at least one sensor in the plurality of sensors is coupled electrically or mechanically to the primary substrate.

11. The method of claim 9, wherein the plurality of sensors include gas sensors and wherein at least one flow hood of the plurality of flow hoods is disposed on a top surface of at least one gas sensor in the plurality of gas sensors disposed on the primary substrate.

12. The method of claim 9, wherein the plurality of sensors are gas sensors and wherein collecting the environmental metric at the sensor point corresponding to the location of at least one gas sensor in the plurality of gas sensors includes using a secondary substrate, wherein the secondary substrate is disposed on a top surface of at least one flow hood in the manifold.

13. The method of claim 9, wherein the sensors are gas sensors and wherein the primary substrate includes a plurality of gas sensor modules, wherein each gas sensor module is configured to couple to a gas sensor.

14. The method of claim 9, wherein the plurality of sensors is a plurality of gas sensors and wherein actively controlling the flow of fluid through the manifold includes pushing or pulling a fluid across a top surface of a gas sensor of the plurality of gas sensors through a flow hood disposed on the top surface of the gas sensor.

15. The method of claim 9, wherein the plurality of sensors is a plurality of gas sensors and wherein actively controlling the flow of fluid through the manifold includes actively controlling a plurality of fluid flows by pushing or pulling a fluid across a top surface of each of the plurality of gas sensors through a flow hood disposed on the top surface of each of the plurality of gas sensors.

16. The method of claim 15, wherein the plurality of sensors is a plurality of gas sensors and wherein pushing or pulling the fluid across the top surface of each of the plurality of gas sensors through the flow hood disposed on the top surface of each of the plurality of gas sensors comprises using a pump system.

17. The method of claim 9, wherein the plurality of sensors is a plurality of gas sensors and wherein a secondary substrate on a given flow hood is configured to capture an environmental metric at a sensor point corresponding to a location of the gas sensor on which the given flow hood is disposed.

18. The method of claim 9, wherein the primary substrate includes a connector and further comprising coupling a device to the primary substrate using the connector.

\* \* \* \* \*